United States Patent
Shulze et al.

(10) Patent No.: US 6,364,847 B1
(45) Date of Patent: Apr. 2, 2002

(54) BLOOD SAMPLING DEVICE

(75) Inventors: John E. Shulze, Rancho Santa Margarita; Douglas R. Savage, San Diego, both of CA (US)

(73) Assignee: Sunscope International, Inc., Newport Beach, CA (US)

( * ) Notice: Subject to any disclaimer, the term of this patent is extended or adjusted under 35 U.S.C. 154(b) by 0 days.

(21) Appl. No.: 09/415,036

(22) Filed: Oct. 7, 1999

(51) Int. Cl.$^7$ .................................................. A61B 10/00
(52) U.S. Cl. ......................... 600/573; 600/580; 604/317
(58) Field of Search .................................. 600/573, 578, 600/411; 604/411

(56) References Cited

U.S. PATENT DOCUMENTS

| | | | |
|---|---|---|---|
| 4,673,386 A | | 6/1987 | Gordon |
| 5,135,489 A | | 8/1992 | Jepson et al. |
| 5,374,401 A | | 12/1994 | von Berg |
| 5,531,711 A | | 7/1996 | Attermeirer et al. |
| 5,536,262 A | | 7/1996 | Velasquez |
| 5,549,569 A | * | 8/1996 | Lynn et al. ............... 604/191 |
| 5,549,577 A | | 8/1996 | Siegel et al. |
| 5,568,260 A | | 10/1996 | Desecki et al. |
| 5,575,769 A | | 11/1996 | Vaillancourt |
| 5,759,160 A | | 6/1998 | Neese et al. |
| 5,785,692 A | | 7/1998 | Attermeier et al. |
| 5,797,897 A | | 8/1998 | Jepson et al. |

* cited by examiner

Primary Examiner—John P. Lacyk
Assistant Examiner—Pamela L Wingood
(74) Attorney, Agent, or Firm—Stout, Uxa, Buyan & Mullins, LLP; Donald E. Stout

(57) ABSTRACT

A blood sampling device is provided for mounting on a patient's forearm or other suitable body location, which incorporates an admixture reservoir and a closed blood sampling cavity in a single housing, the functional elements of which are firmly mounted and easily accessible to the caregiver. The blood sampling cavity is preferably accessed by a blunt cannula, which is readily retained in the sampling cavity by virtue of the cavity's secured position and elevated location on the sampling device housing during the sampling procedure, without the need for a cannula locking device. The sampling device of the present invention incorporates an admixture reservoir having a rotary actuator, through which the internal fluid volume of the admixture reservoir is manipulated from nil to a volume which is sufficient to remove all admixture from the blood sampling cavity during a sampling procedure, thus insuring that a clean blood sample may be withdrawn by an aspiration device attached to a sterile blunt cannula which penetrates a split septum of the blood sampling cavity. In a preferred embodiment, the internal surface of the admixture reservoir, which contacts a flexible stopper portion of the actuator, is provided with a curved shape which causes the outer edges of the flexible stopper to first contact the reservoir walls, followed subsequently by wall contact with increasingly more central interior portions of the stopper, and finally through contact and sealing of a central exit port in the reservoir, such that all admixture is urged from the walls of the reservoir as the reservoir is closed.

23 Claims, 2 Drawing Sheets

BLOOD SAMPLING DEVICE

BACKGROUND OF THE INVENTION

This invention relates to medical devices, and more particularly to an improved blood sampling device which is mountable on a patient's forearm or other suitable body location, and which incorporates an admixture reservoir and a closed blood sampling cavity in a single housing.

During the care of critically ill patients and those patients undergoing major surgical procedures, it is common practice to insert one or more catheters into blood vessels of the patient's cardiovascular circulatory system. These catheters are then used to perform continuous direct, invasive blood pressure monitoring, for delivery of medications or nutrients, and for collection of blood samples to be submitted for laboratory analysis.

The medical staff conducting the procedure might obtain such blood samples by connecting a syringe or other aspirating device, and a shutoff valve directly to the proximal end of a catheter lumen, the distal end of which lies in a patent blood vessel or other chamber containing blood within the body.

But since such catheters represent a communication route to the central circulatory system, careful sample site handling procedures and closed system sampling fittings are often used to minimize the chance for transmission of infection to or from the patient during blood sampling from vascular catheters. Research has shown that a reduction in catheter infection rates can be achieved while simultaneously reducing exposure of the caregiver and other third parties to the patients' blood, simply by reducing the number of times the catheter ports are opened to the external environment during the course of patient care.

Thus, devices have been developed for blood sampling and/or injection of medications into an otherwise closed fluid-filled cavity which is in communication with a catheter lumen. Devices which use a blunt penetration cannula to enter the cavity (see, for example, published PCT Application No. WO 89/06553) are preferred because they greatly reduce the chance of accidental needle stick injury and the resulting potential for transmission of infections to the caregiver.

When it is important to obtain an undiluted blood sample for laboratory analysis, the cavity must generally be purged of medication and/or other fluids being infused through the catheter lumen. To avoid aspirating and discarding the blood/fluid admixture contained in the cavity, in line reservoirs have been developed to pump away and temporarily store the admixture while a sample of pure blood is drawn off from the cavity (see, for example, U.S. Pat. No. 5,135, 489). After the sample is obtained, the reservoir is emptied, returning the admixture to the cavity and catheter, where it is subsequently returned to the patient's bloodstream. Such reservoir devices are preferable because they minimize the patients' blood loss, while reducing the creation of biological waste in the critical care environment.

However, currently available blood sampling systems are difficult to use. A common mounting location for blood sampling systems is on a patient's forearm, adjacent a radial artery catheterization site. Two separate devices, a blood sampling cavity, and an admixture storage reservoir, must be placed in series in the tubing connected to the catheter, running along the patients' forearm. A practically sized reservoir to aspirate enough admixture to obtain a clean blood sample is sufficiently large that the reservoir is often taped or strapped to the forearm.

Thus, the second device, the blood sampling cavity, is often allowed to flop around freely, juxtapositioned between the reservoir and the proximal end of the catheter. However, since it is unsecured, the chances of accidental contact between the split septum surface of the blood sampling device, the patient's skin, and other contaminating objects is ever present. And because the cavity is unsecured, it has been considered necessary to develop locking mechanisms to firmly attach the blunt cannula to the cavity (see for example U.S. Pat. No. 5,797,897) during the blood sampling procedure.

In known prior art devices, when a caregiver wishes to use the admixture storage reservoir to remove admixture from the cavity, an actuator device on the reservoir must be pulled away from the reservoir and/or patient's arm, possibly causing patient discomfort. Even when the reservoir is empty, the protruding actuator lies above the reservoir, creating the potential that the actuator may become entangled in other tubing, electrocardiogram lead wires, or the patient's clothing.

In some other prior art devices, the reservoir has been moved to a mounting plate disposed on an intravenous (IV) pole adjacent to the patient's bed to avoid the above mentioned difficulties. However, since the blood sampling cavity must still be located close to the end of the catheter on the patient's forearm to obtain clean blood samples with reasonably sized admixture reservoirs, these two devices, which must both be manipulated during a blood sampling procedure, are separated by a distance of at least several feet; thus increasing the difficulty of the sampling procedure, and the chance for procedural errors.

Also, in state-of-the-art blood sampling devices, there is always the possibility for formation of small blood clots on the interior walls of the reservoir during sampling, depending variably on the mixture of blood and other fluids that have been pumped from the catheter and the blood sampling cavity. Unfortunately, prior art devices do not contain any active means to ensure that all blood and fluid is urged from the walls of the reservoir after each blood sampling procedure. Thus a thin layer of clotted blood on the reservoir walls can build up with repeated use.

To make the blood sampling procedure as quick and safe as possible for the caregiver and the patient, there is, therefore, a need for an improved blood sampling device which is easily mounted to a patient's forearm or other body location, without protruding actuator mechanisms which might become entangled in the patient's clothes or other cables and tubes which may be positioned in close proximity to the patient.

There is a further need for a more secure mounting of the blood sampling cavity to reduce the chance for contamination of the split septum surface which is to be penetrated by the blunt cannula, and to reduce the need for a locking device to secure the blunt cannula.

Further, there is a need for an arm-mounted blood sampling device with an improved actuator which does not require the care giver to pull the actuator in a direction away from the body of the reservoir.

It would also be highly desirable to develop a compact blood sampling device which can be comfortably worn on a patient's forearm, incorporates all required components in one low cost assembly housing with a minimum number of parts, and which occupies a minimum vertical height when the reservoir is empty, while also elevating and securing the position of the blood sampling cavity and split septum sampling site above the forearm for easier access by the caregiver during the blood sampling procedure.

Finally, it would be highly desirable to provide an admixture reservoir with minimal deadspace volume when closed and an active means to urge any remaining fluid or platelets from the internal walls of the reservoir, such that they might be fully returned to the catheter and cavity when the reservoir is closed.

SUMMARY OF THE INVENTION

In accordance with the present invention, an improved blood sampling device is provided for mounting on a patient's forearm or other suitable body location, which incorporates an admixture reservoir and a closed blood sampling cavity in a single housing, the functional elements of which are firmly mounted and easily accessible to the caregiver. The blood sampling cavity is preferably accessed by a blunt cannula, which is readily retained in the sampling cavity by virtue of the cavity's secured position and elevated location on the sampling device housing during the sampling procedure, without the need for a cannula locking device. The sampling device of the present invention incorporates an admixture reservoir having a rotary actuator, through which the internal fluid volume of the admixture reservoir is manipulated from nil to a volume which is sufficient to remove all admixture from the blood sampling cavity during a sampling procedure, thus insuring that a clean blood sample may be withdrawn by an aspiration device attached to a sterile blunt cannula which penetrates a split septum of the blood sampling cavity. In a preferred embodiment, the internal surface of the admixture reservoir, which contacts a flexible stopper portion of the actuator, is provided with a curved shape which causes the outer edges of the flexible stopper to first contact the reservoir walls, followed subsequently by wall contact with increasingly more central interior portions of the stopper, and finally through contact and sealing of a central exit port in the reservoir, such that all admixture is urged from the walls of the reservoir as the reservoir is closed.

More particularly, in one aspect of the invention, a blood sampling device is provided, which has a fluid flow path extending therethrough. The fluid flow path has a proximal end and a distal end, the proximal end being adapted for communication with a fluid supply and the distal end being adapted for communication with a catheter placed in a blood vessel. The blood sampling device comprises a fluid storage reservoir having interior walls which define a variable volume, which volume is variable between substantially nil and a maximum volume. An aperture is disposed between the fluid flow path and the fluid storage reservoir, for permitting fluid communication between the fluid flow path and the fluid storage reservoir. A blood sampling cavity is disposed in the blood sampling device, and a split septum is disposed on a wall defining the blood sampling cavity, for sealingly engaging a blunt cannula for the purpose of aspirating blood from the blood sampling cavity.

In another aspect of the invention, there is provided a blood sampling device which has a fluid flow path extending therethrough. The fluid flow path has a proximal end and a distal end, the proximal end being adapted for communication with a fluid supply and the distal end being adapted for communication with a catheter placed in a blood vessel. The blood sampling device comprises a housing, in which the fluid flow path is disposed, and a fluid storage reservoir having a variable volume, which is also disposed in the housing. The reservoir volume is variable between substantially nil and a maximum volume. An actuator is provided for varying the volume of the fluid storage reservoir. Advantageously, an external dimension, preferably height, of the blood sampling device varies in proportion to the variance of the volume of the fluid storage reservoir, such that the external dimension is at a substantial maximum when the volume of the reservoir is at its maximum volume, and at a substantial minimum when the volume of the reservoir is substantially nil. This ability is accomplished by the use of a rotary actuator for varying the volume, which does not extend below the housing when rotated to its most advanced position, corresponding to nil volume, thereby avoiding potential entanglements with clothing, fluid lines, and the like, and does extend below the housing when rotated to a retracted position, corresponding to a substantial volume. When extended, the actuator acts against an adjacent supporting structure, such as a wrist strap, to elevate the split septum and associated blood sampling cavity on the blood sampling device above any adjacent device mounting surface or securement means, so that access to the split septum is eased for the procurement of a blood sample.

In still another aspect of the invention, a blood sampling device is provided, which comprises a fluid flow path extending therethrough. The fluid flow path has a proximal end and a distal end, the proximal end being adapted for communication with a fluid supply and the distal end being adapted for communication with a catheter placed in a blood vessel. A fluid storage reservoir is provided which has interior walls defining a variable volume, which volume is variable between a predetermined minimum volume and a predetermined maximum volume. An aperture is disposed between the fluid flow path and the fluid storage reservoir, for permitting fluid communication between the fluid flow path and the fluid storage reservoir. A movable stopper is disposed in the reservoir for varying the volume. Importantly, one of the interior wall and the movable stopper is flexible in order to actively urge all fluid and blood from the volume after a blood sampling procedure. In the preferred embodiment, it is the stopper which is flexible.

In still another aspect of the invention, a blood sampling device is provided, which has a fluid flow path extending therethrough. The fluid flow path has a proximal end and a distal end, the proximal end being adapted for communication with a fluid supply and the distal end being adapted for communication with a catheter placed in a blood vessel. A fluid storage reservoir is disposed in the device, having an interior wall which defines a volume for containing fluid, which volume is variable between a predetermined minimum volume and a predetermined maximum volume. An aperture is disposed between the fluid flow path and the fluid storage reservoir, for permitting fluid communication between the fluid flow path and the fluid storage reservoir. A movable stopper is disposed in the reservoir for varying the volume. Advantageously, upper portions of the reservoir interior wall adjacent to the aperture are curved in order to actively encourage evacuation of all fluids from the reservoir.

In still another aspect of the invention, a system for invasive pressure monitoring of a patient is provided, which uses direct radial arterial cannulation. The system comprises a blood pressure transducer adapted for disposition on an upper portion of a patient's arm, and a blood sampling device. The blood sampling device has a fluid flow path extending therethrough. The fluid flow path has a proximal end and a distal end, the proximal end being adapted for communication with a pressure monitoring line which also communicates with a distal port on the blood pressure transducer. The distal end is adapted for communication with a catheter placed in a blood vessel. The blood sampling device comprises a fluid storage reservoir having interior walls which define a variable volume, which volume is variable between substantially nil and a maximum volume. An aperture is disposed between the fluid flow path and the fluid storage reservoir, for permitting fluid communication between the fluid flow path and the fluid storage reservoir. A blood sampling cavity is disposed in the blood sampling device, and a split septum is disposed on a wall defining the blood sampling cavity, for sealingly engaging a blunt cannula for the purpose of aspirating blood from the blood sampling cavity.

In another aspect of the invention, there is disclosed a method for sampling the blood of a patient using a radial artery catheter which has been inserted into an artery of the patient. The method comprises first the step of interrupting any fluid which is being infused into the patient through a fluid line which is attached to the catheter. Then, a volume of a fluid storage reservoir which is contained in a blood sampling device which is disposed in the fluid line is increased from a substantially nil volume to a greater volume, wherein a blood sampling cavity is in fluid communication with the fluid line, and the fluid storage reservoir is in fluid communication with the blood sampling cavity, so that any fluid admixture contained in the blood sampling cavity flows into the fluid storage reservoir. This step of increasing the volume also functions to raise a height of a housing containing the fluid storage reservoir and the blood sampling cavity, thereby raising a height of a split septum disposed on the housing. Following this, a distal end of a cannula is inserted into the split septum, and blood is withdrawn from the blood sampling cavity through the cannula into a syringe attached to a proximal end of the cannula. Following this, the volume of the fluid storage reservoir is decreased and the cannula is removed from the split septum.

An improved and easier to use blood sampling procedure for use with the present invention, which maintains a closed blood sampling system for mutual protection of the patient and caregiver is described.

The invention, together with additional features and advantages thereof, may best be understood by reference to the following description taken in conjunction with the accompanying illustrative drawing.

DESCRIPTION OF THE PREFERRED

Figure 1:
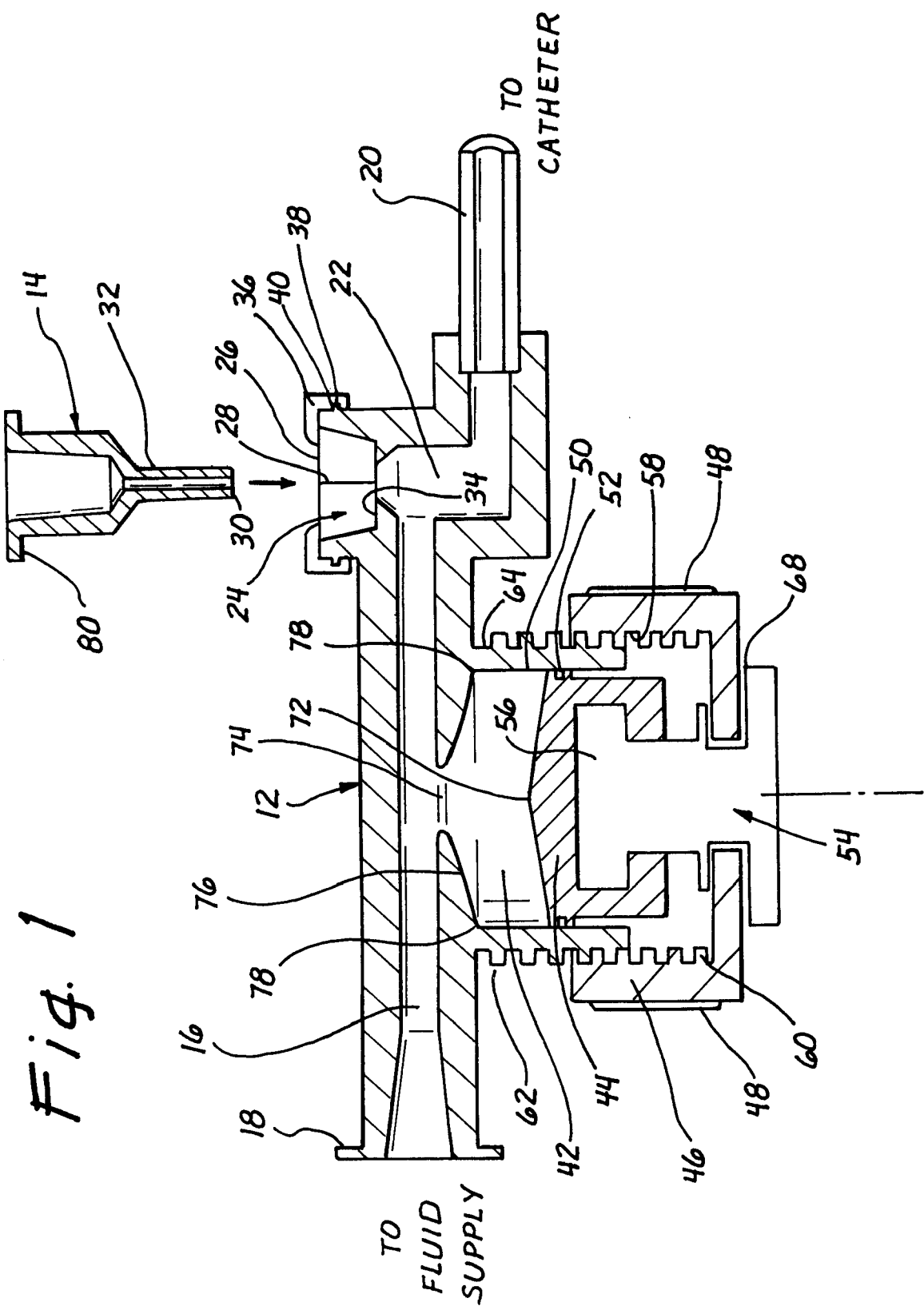
FIG. 1 is a cross-sectional view of a preferred embodiment of the blood sampling device and blunt cannula constructed in accordance with the present invention.

Referring now more particularly to the drawings, there is shown in FIG. 1 a preferred embodiment of a blood sampling device 10 of the present invention, comprising a housing 12 and a blunt cannula 14. The housing 12 includes a liquid channel 16 extending from a proximal Luer connector 18 to a distal tubing segment 20. The proximal Luer connector 18 is typically connected to a source of sterile fluid and/or medication to be infused into a patient. The distal tubing segment 20 is typically connected to a lumen of a catheter for infusing solutions and/or medications into a patient's bloodstream. Thus, liquid to be infused into the patient's bloodstream normally travels from the fluid supply via the proximal Luer connector 18, traverses the liquid channel 16, and passes through a blood sampling cavity 22. Then the liquid to be infused flows through the distal tubing segment 20 to the catheter lumen, and ultimately to the distal end of the catheter lumen where it enters the patient's blood stream.

Further included in the housing 12 is a split septum 24, through which the blunt cannula 14 may be inserted to access the fluid contained in the blood sampling cavity 22. The split septum 24 is preferably made from a flexible material like polyisoprene or natural rubber, so that as the cannula 14 is pressed against an external surface 26 of the split septum 24 in the vicinity of a slit 28 therein, the flexible material will grasp and sealingly engage the blunt cannula. As the blunt cannula 14 is advanced further, the tip 30 of the cannula will enter the blood sampling cavity 22, while a seal is maintained around the shaft 32 of the blunt cannula 14. The split septum 24 is sealingly retained in a recess 34 in the housing 12 by a snap-on cap 36. The snap-on cap 36 is retained on the housing 12 by a raised annular ring 38 on the surface of the housing which engages a mating annular groove 40 on the inner diameter of the snap-on cap 36.

Still with particular reference to FIG. 1, a fluid storage reservoir 42 is disposed in the housing 12, in fluid communication with the liquid channel 16. On one side of the fluid storage reservoir 42 is disposed a flexible stopper 44. The flexible stopper 44 is engaged by a rotating actuator knob 46, having raised gripping ribs 48 on its outer circumference, to advance or retract the flexible stopper 44 along a cylindrically shaped channel 50 which forms the walls of the fluid storage reservoir 42. The flexible stopper 44 is generally round in shape when viewed from the end facing the liquid channel 16, with raised annular sealing rings 52 conforming to the shape of the cylindrically shaped channel 50. A pushrod 54, made from a somewhat stiffer material than that of the stopper 44, retains the stopper 44 about a head portion 56 thereof, and transmits forward or rearward force generated by the rotating actuator knob 46 to advance or retract the flexible stopper 44 into or out of the fluid storage reservoir 42. With this arrangement, the internal volume of the fluid storage reservoir 42 can be varied from nil to a maximum volume of 2–10 cc. The rotating actuator knob 42 is preferably generally round in shape when viewed from the direction of the liquid channel 16. Along its inner walls 58 is preferably disposed a helical thread 60 which is adapted to engage a compatible helical thread 62 on outer walls 64 of the portion of the housing 12 which defines the fluid storage reservoir 42.

Figure 2:
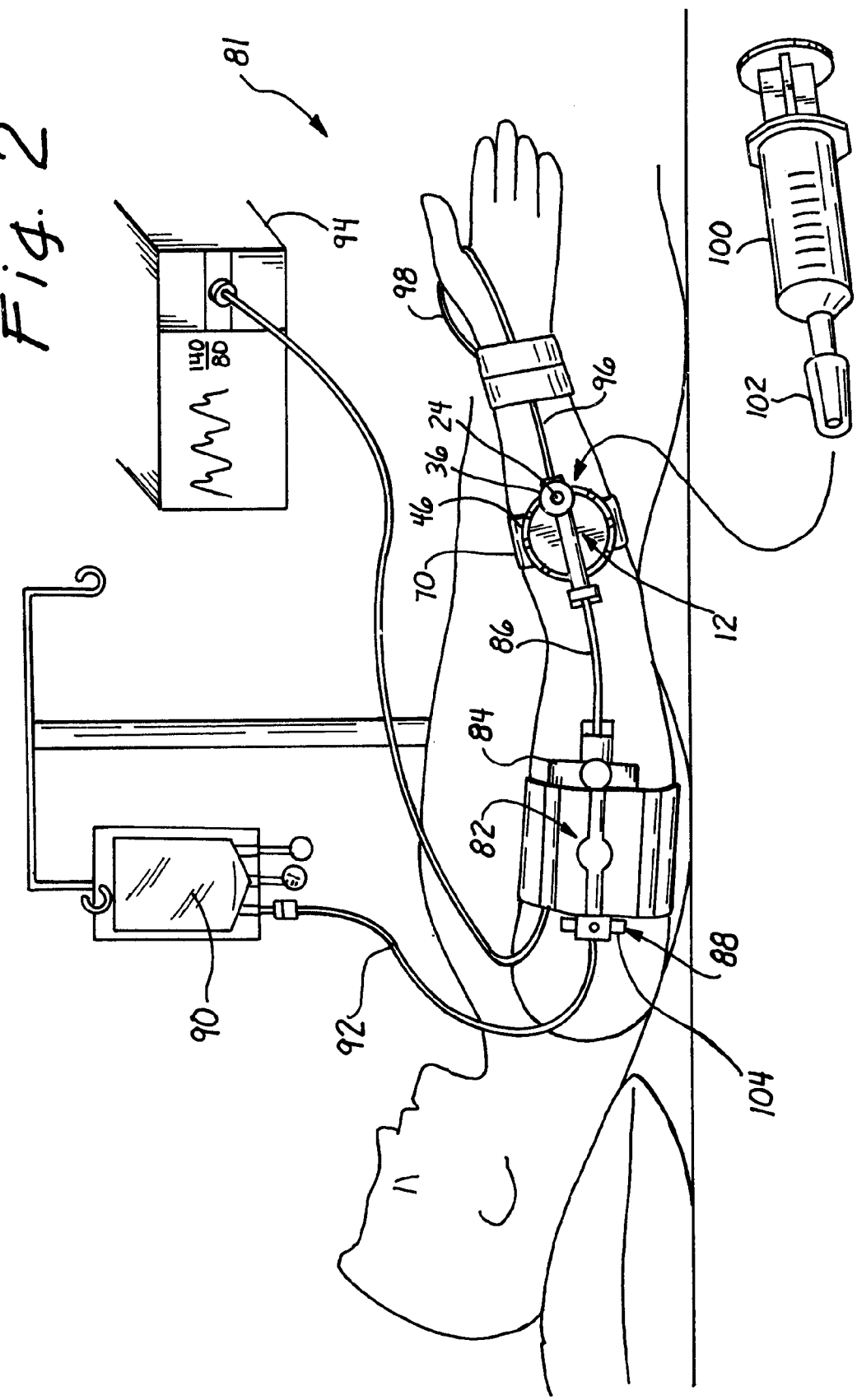
FIG. 2 is a schematic illustration of the blood sampling device of the present invention, as it might be employed on a patient in a critical care setting, when used in conjunction with a pressure monitoring system, including a medicated fluid supply, pressure transducer, flush device, and catheter.

Thus, when the rotating actuator knob 46 is rotated around a longitudinal axis 66 of the pushrod 54, the force generated by the engagement of the helical threads 60 and 62 in either the forward or rearward direction, along the axis 66, is transmitted through the pushrod 54 to the flexible stopper 44, as described supra. There is a small amount of mechanical clearance space 68 between the pushrod 54 and the rotating actuator knob 46, and sufficient frictional engagement between the flexible stopper 44 and the fluid storage reservoir walls 58, such that the pushrod 58 does not rotate with the rotating actuator knob 46. Thus, the bottom portion of the pushrod 58 can be fixed, if desired, to a stationary mounting bracket or wrist mounting strap 70 as is shown in FIG.2.

The compatible external helical thread 62 preferably contains a stop thread detent (not shown) at its rearwardmost extent from the housing. Thus, the actuator 46 cannot be easily unscrewed further when the fluid storage reservoir has reached its maximum rated volume by turning of the rotating actuator means, so that the pushrod 54 is fully retracted, because of the stop thread detent. In a preferred embodiment, the helical thread 60 and compatible housing thread 62 are together arranged such that the care giver, when viewing the blood sampling device 10 from the top, can rotate the rotating actuator knob 46, with thumb and forefinger, in the counterclockwise direction to increase the volume of the fluid storage reservoir 42, and clockwise to decrease the volume of the reservoir.

The flexible stopper 44 has a raised center apex 72 which is located along an extension of the central axis 66 of the pushrod, and the apex is designed to matingly engage an aperture 74 where the fluid storage reservoir 42 is in fluid communication with the liquid channel 16, when the pushrod 54 has been fully advanced to reduce the volume of the reservoir to nil. This is accomplished by rotating the rotating actuator knob 46 until the helical threads 60 have fully engaged the compatible helical threads 62 on the fluid storage reservoir portion of the housing 12. As the flexible stopper 44 nears contact with the aperture 74, being urged along by the pushrod 54, the walls 58 of the fluid storage reservoir 42 in the vicinity of the aperture are shaped in a receding curve, such that the stopper first engages the upper walls 76 at their outermost edges 78, away from the aperture 74. As the stopper 44 compresses against the outermost edges 78, any fluid or blood components remaining between the flexible stopper 44 and the upper walls 76 are urged toward the aperture 74. As the stopper 44 continues to press forward, its shape changes such that it conforms to the receding surface of the upper walls, thus continuing the process of urging any remain fluid or blood towards the central aperture 74. Finally, the flexible stopper 44 takes on the shape of the upper walls 76 and the aperture 74, thus reducing the volume of the fluid storage reservoir 42 to nil and forming a smooth flexible sealing plug along the wall of the liquid channel 16 at the location of the aperture.

Still with reference to FIG. 1, the blunt cannula 14 is preferably shaped to matingly engage a blood sampling syringe, for example, by inclusion of a female Luer connector 80. Preferably, all components for the device 10, except for the flexible stopper 44, distal tubing segment 20, and split septum 24, are molded from biocompatible structural plastics, such as polycarbonate, polystyrene, etc, as is well known in the injection molding art. The aforementioned flexible stopper, distal tubing segment, and split septum (neoprene rubber, polyurethane, polyisoprene, flexible PVC, etc) are preferably molded using a more flexible range of biocompatible polymers, such as neoprene rubber, polyurethane, polyisoprene, and flexible PVC and the like. The blood sampling device 10 and blunt cannula 14 are preferably supplied sterile, for one time disposable use.

Now with reference particularly to FIG. 2, there is shown a system 81 for invasive pressure monitoring of an intensive care unit (ICU) or surgical patient, using direct radial arterial cannulation. The system 81 includes a blood pressure transducer 82, such as one which is disclosed in copending U.S. patent application No. 08/844,236, herein expressly incorporated by reference. The system 81 further includes an integral 3-way zeroing stopcock 84, a pressure monitoring line 86, a flush device 88, a pressurized saline infusion bag 90, an intravenous (IV) administration set 92, a blood pressure monitor 94, and distal extension tubing 96 taped to the patient's wrist and secured to a radial artery catheter (cannula), not shown but located under the wrist strap 70. A service loop 98 is present in the distal tubing extension to minimize strain on the catheter puncture site and the radial artery. The blood pressure transducer 82 is attached to the patient's upper arm using a strap or tape. These devices are well known in the art of monitoring critically ill patients.

A preferred embodiment of the blood sampling device of the present invention 10 is positioned on the patient's forearm and located in the path of infusion fluid flow between the pressure monitoring line 86 and the distal extension tubing 96. The blood sample reservoir 42 must be large enough to pump sufficient admixture from the above components to introduce pure blood from the patient's blood stream into the blood sample cavity 22, yet small enough to fit comfortably on the patient's forearm during routine monitoring of the patient. This is accomplished in the current invention by a unique design of reservoir/actuator housing 12, wherein in the normal monitoring position, the rotating actuator knob 46 is in its fully clockwise position, with the fluid storage reservoir 42 fully closed, having nil volume, and the height of the blood sampling device is minimized with no projections of the actuator above the level of the reservoir.

However, when the reservoir is fully filled with stored fluid, and the blood sampling cavity filled with pure blood, the height of the sampling device is increased for easy and sturdy access to the split septum blood sampling site. In this mode, the blunt cannula 14 has been attached to a blood sampling syringe 100 (FIG. 2), which will be used to transport the blood sample to the laboratory for analysis. Covering the tip of the blunt cannula is a cap 102. To take a pure blood sample from the blood sampling device 10, the infusion fluid must first be interrupted in the tubing and catheter, and the admixture removed from the blood sampling cavity 22, distal extension tube 96, and cannula 14. This is accomplished by first turning off the 3-way stopcock 84 and interrupting monitoring and infusion from the flush device 88, thus blocking flow from leaving or entering the proximal end of monitoring line 86. The rotating actuator knob 46 is rotated counterclockwise to the extent of its rotational travel between thumb and forefinger, thereby increasing the volume of the fluid storage reservoir 42 and raising the height of the housing 12 and split septum 24. The split septum 24 is then wiped with a pledget (not shown) containing isopropyl alcohol or other disinfectant, the cap 102 is removed from the blunt cannula 14, and the cannula with syringe 100 attached is pushed into the blood sample cavity 22 through the split septum 24. With the split septum sealingly engaging the blunt cannula and syringe in position above the sampling device 10, a pure blood sample is withdrawn into the syringe 100. While holding the syringe and blunt cannula in position in the blood sample cavity, the rotating actuator knob 46 is rotated fully clockwise to return the admixture to the blood sample cavity and the catheter. A small amount of pure blood is expelled from the blunt cannula 14 by pushing on the syringe barrel, then the blunt cannula and syringe are removed from the blood sample cavity and re-capped. The split septum 24 is again wiped with the alcohol pledget and the pledget is discarded. The 3-way stopcock 84 is returned to the normal monitoring position (OFF to the zero port) and the system is returned to normal infusion and pressure monitoring status. A fast flush valve 104 on the flush device 88 is momentarily activated to remove any remaining blood from the catheter. The syringe 100 with capped blunt cannula 14 attached is transported to the laboratory for analysis. Thus has been shown a much more convenient method for blood sampling using a completely closed sampling system where the care giver is not exposed to the patient's blood, and the internal lumens of the catheter have not been exposed to the external environment for possible contamination by airborne pathogens or accidental contact with nonsterile objects. All manipulations of the flush device 88 and blood sample device 10 can be accomplished quickly and easily, because of the co-location of components, with a minimal pulling on the connecting tubing or tape or straps attached to the patient. The inventive blood sampling device is comfortable to wear, with a minimum height and no vertical protruding actuators when the device is in not in use. Thus it is safer for the patient, with less potential for entanglement in tubes, wires, or clothing surrounding the patient.

It should be noted that it is within the scope of the invention to combine the structure of the blood sampling device 10 and the blood pressure transducer 82, if desired. In such an instance, there would be a single housing accommodating all of the elements presently shown and disclosed in connection with the device 10 and the transducer 82, for the purpose of reducing the number of elements and components which would be attached to the patient, and reducing related costs and complexity.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A system for invasive pressure monitoring of a patient, using direct radial arterial cannulation, comprising:
    a blood pressure transducer adapted for disposition on an upper portion of a patient's arm; and
    a blood sampling device, having a fluid flow path extending therethrough, said flowpath having a proximal end and a distal end, the proximal end being adapted for communication with a pressure monitoring line which also communicates with a distal port on said blood pressure transducer, and said distal end being adapted for communication with a catheter placed in a blood vessel, said blood sampling device comprising:
        a fluid storage reservoir having interior walls which define a variable volume, said volume being variable between substantially nil and a maximum volume;
        an aperture disposed between said fluid flow path and said fluid storage reservoir, for permitting fluid communication between said fluid flow path and said fluid storage reservoir;
        a blood sampling cavity; and
        a split septum disposed on a wall defining said blood sampling cavity, for sealingly engaging a blunt cannula for the purpose of aspirating blood from the blood sampling cavity.

2. A method for sampling blood of a patient using a radial artery catheter which has been inserted into an artery of the patient, the method comprising:
    interrupting any fluid which is being infused into the patient through a fluid line which is attached to the catheter;
    increasing a volume of a fluid storage reservoir contained in a blood sampling device which is disposed in said fluid line from a substantially nil volume to a greater volume, wherein a blood sampling cavity is in fluid communication with said fluid line, and said fluid storage reservoir is in fluid communication with said blood sampling cavity, so that any fluid admixture contained in said blood sampling cavity flows into said fluid storage reservoir, wherein the step of increasing said volume also raises a height of a housing containing said fluid storage reservoir and said blood sampling cavity, thereby raising a height of a split septum disposed on said housing;
    inserting a distal end of a cannula into said split septum;
    withdrawing blood from said blood sampling cavity through said cannula into a syringe attached to a proximal end of said cannula;
    decreasing the volume of said fluid storage reservoir so that the fluid admixture disposed in said fluid storage reservoir is returned to said blood sampling cavity; and
    removing the cannula from said split septum.

3. A blood sampling device, having a fluid flow path extending therethrough, said flowpath having a proximal end and a distal end, the proximal end being adapted for communication with a fluid supply and the distal end being adapted for communication with a catheter placed in a blood vessel, said blood sampling device comprising:
    a housing, said fluid flow path being disposed therein;
    fluid storage reservoir having a variable volume and being disposed in said housing, said volume being variable between substantially nil and a maximum volume; and
    an actuator for varying the volume of said fluid storage reservoir, said actuator comprising a rotating actuator knob;
        wherein an external dimension of said blood sampling device varies in proportion to the variance of the volume of said fluid storage reservoir, said external dimension being at a substantial minimum when the volume of said fluid storage reservoir is substantially nil, and said external dimension being at a substantial maximum when the volume of said reservoir is at said maximum volume.

4. The blood sampling device as recited in claim 3, wherein said knob includes threads which engage corresponding threads on said fluid reservoir, said threaded engagement permitting said rotating knob to rotate in either direction, whereby the knob may be advanced or retracted relative to said fluid reservoir as desired in order to correspondingly decrease or increase the volume of said fluid reservoir.

5. A blood sampling device, comprising:
    a housing having a fluid flow path extending therethrough, said flowpath having a proximal end and a distal end, the proximal end being adapted for communication with a fluid supply and said distal end being adapted for communication with a catheter placed in a blood vessel;
    a fluid storage reservoir disposed in said housing and having interior walls which define a variable volume, said volume being variable between substantially nil and a maximum volume;
    an aperture disposed between said fluid flow path and said fluid storage reservoir, for permitting fluid communication between said fluid flow path and said fluid storage reservoir;
    a blood sampling cavity disposed in said housing; and
    a split septum disposed on a wall of said housing which defines said blood sampling cavity, for sealingly engaging a blunt cannula for the purpose of aspirating blood from the blood sampling cavity.

6. The blood sampling device as recited in claim 5, and further comprising a movable stopper for varying the volume of said fluid storage reservoir.

7. The blood sampling device as recited in claim 6, and further comprising an actuator for retracting and advancing said stopper out of and into said reservoir, to thereby vary the volume of said reservoir.

8. The blood sampling device as recited in claim 7, wherein said actuator comprises a rotating actuator knob.

9. The blood sampling device as recited in claim 8, wherein said knob is connected to said stopper and includes threads which engage corresponding threads on said fluid reservoir, said threaded engagement permitting said rotating knob to rotate in either direction, whereby the knob may be advanced or retracted relative to said fluid reservoir as desired in order to correspondingly advance or retract said stopper.

10. The blood sampling device as recited in claim 9, and further comprising a pushrod for connecting said rotating knob to said stopper.

11. The blood sampling device as recited in claim 6, wherein said stopper is fabricated of a flexible material.

12. The blood sampling device as recited in claim 11, wherein the interior walls of said fluid reservoir are shaped in a receding curve near said aperture, so that said flexible stopper first engages upper portions of said walls at outermost edges thereof, away from said aperture, as it is advanced, following which the flexible stopper changes its configuration as it continues to advance, conforming to the receding surface of said upper portions of said walls in order to urge all residual blood or fluid from said reservoir through said aperture.

13. The blood sampling device as recited in claim 5, wherein the wall of said housing in which said split septum is disposed also defines said blood storage reservoir.

14. The blood sampling device as recited in claim 5, said housing being a molded integral structure.

15. A blood sampling device, having a fluid flow path extending therethrough, said flowpath having a proximal end and a distal end, the proximal end being adapted for communication with a fluid supply and the distal end being adapted for communication with a catheter placed in a blood vessel, said blood sampling device comprising:

a fluid storage reservoir having a variable volume which is defined by outer walls, said volume being variable between substantially nil and a maximum volume; and an actuator for varying the volume of said fluid storage reservoir;

wherein an external dimension of said reservoir outer walls varies in proportion to the variance of the volume of said fluid storage reservoir, said external dimension being at a substantial minimum when the volume of said fluid storage reservoir is substantially nil, and said external dimension being at a substantial maximum when the volume of said reservoir is at said maximum volume.

16. The blood sampling device as recited in claim 15, and further comprising a movable stopper for varying the volume of said fluid storage reservoir, said actuator being connected to said movable stopper.

17. The blood sampling device as recited in claim 16, wherein said movable stopper is flexible.

18. The blood sampling device as recited in claim 15, wherein said external dimension of said reservoir outer walls is a height of said outer walls, whereby said blood sampling device is compact when the reservoir is empty, to avoid entanglement with a patient's clothing or other items, and is at said substantially maximum height when the reservoir is substantially full, so that easy and sturdy access to a blood sampling site is enabled.

19. The blood sampling device as recited in claim 15, wherein said actuator is located below said fluid flow path.

20. The blood sampling device as recited in claim 15, wherein said blood sample cavity moves upwardly as the volume of said fluid storage reservoir is increased.

21. The blood sampling device as recited in claim 16, and further comprising a pushrod connected to said stopper.

22. The blood sampling device as recited in claim 15, wherein there is no plunger structure disposed in said blood sampling device which moves axially relative to said reservoir outer walls or extends axially from said reservoir.

23. A blood sampling device, comprising:

a fluid flow path extending through said device, said flowpath having a proximal end and a distal end, the proximal end being adapted for communication with a fluid supply and the distal end being adapted for communication with a catheter placed in a blood vessel;

a fluid storage reservoir disposed in said device, said fluid storage reservoir having an interior wall which defines a volume for containing fluid, said volume being variable between a predetermined minimum volume and a predetermined maximum volume;

an aperture disposed between said fluid flow path and said fluid storage reservoir, for permitting fluid communication between said fluid flow path and said fluid storage reservoir;

a movable flexible stopper disposed in said reservoir for varying said volume; and said reservoir interior wall having upper portions thereof which are shaped in a receding curve near said aperture, so that said flexible stopper first engages said upper portions of said walls at outermost edges of the stopper, away from said aperture, as it is advanced toward said aperture, followed by successive contact with said interior wall at ever narrowing annular portions of the stopper, and finally at a center region of the stopper, whereupon the aperture is sealed by said stopper.

* * * * *